United States Patent [19]
Gold

[11] Patent Number: 4,976,699
[45] Date of Patent: Dec. 11, 1990

[54] NEEDLE AND SAFETY COVER ASSEMBLY FOR SYRINGES AND THE LIKE

[76] Inventor: Steven K. Gold, 2611 Woodberry Rd., Broomall, Pa. 19008

[21] Appl. No.: 356,241

[22] Filed: May 24, 1989

[51] Int. Cl.$^5$ .............................................. A61M 5/32
[52] U.S. Cl. ...................................... 604/192; 604/263
[58] Field of Search ........................ 604/187, 192, 263

[56] References Cited

U.S. PATENT DOCUMENTS

| | | | |
|---|---|---|---|
| 3,658,061 | 4/1972 | Hall | 128/214.4 |
| 4,643,722 | 2/1987 | Smith, Jr. | 604/192 |
| 4,747,830 | 5/1988 | Gloyer et al. | 604/110 |
| 4,747,835 | 5/1988 | Sandhaus | 604/192 |
| 4,747,836 | 5/1988 | Luther | 604/198 |
| 4,752,290 | 6/1988 | Schramm | 604/198 |
| 4,758,230 | 7/1988 | Ryrcroft | 604/118 |
| 4,758,231 | 7/1988 | Haber et al. | 604/198 |
| 4,762,516 | 8/1988 | Luther et al. | 604/164 |
| 4,767,412 | 8/1988 | Hymanson | 604/192 |
| 4,772,272 | 9/1988 | McFarland | 604/198 |
| 4,778,453 | 10/1988 | Lopez | 604/110 |
| 4,795,443 | 1/1989 | Permenter et al. | 604/110 |
| 4,820,277 | 4/1989 | Norelli | 604/192 |

FOREIGN PATENT DOCUMENTS

| | | | |
|---|---|---|---|
| 3713754 | 4/1987 | Fed. Rep. of Germany | 604/192 |
| 2618685 | 7/1987 | France | 604/192 |

OTHER PUBLICATIONS

Article by R. D. McCormick et al entitled, "Epidemiology of Needle Stick Injuries in Hospital Personnel," The American Journal of Medicine, vol.-70, Apr., 1981, pp. 928-932.
Article entitled "AIDS: Its Impact On the Global Medical Plastics Industry", appearing in Medical Devices and Diagnostic Industry (MD&DI), Apr., 1988; pp. 26-28.

*Primary Examiner*—John D. Yasko
*Attorney, Agent, or Firm*—William Freedman; Morton C. Jacobs

[57] ABSTRACT

A protective cover for a syringe needle which maintains the sterility of the needle prior to use, is easily displaced with one hand in order to employ the syringe in the application of fluid transfer via its needle portion with the same hand, is readily repositioned back over the needle with the same hand, prevents reuse, indicates prior use, prevents accidental needle sticks, and is able to be manufactured cost-effectively.

28 Claims, 8 Drawing Sheets

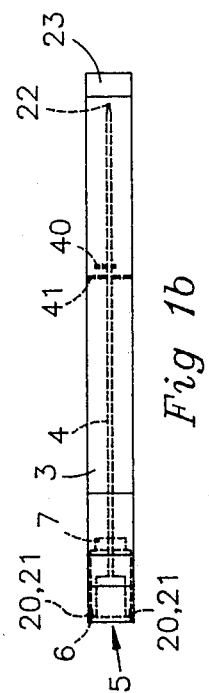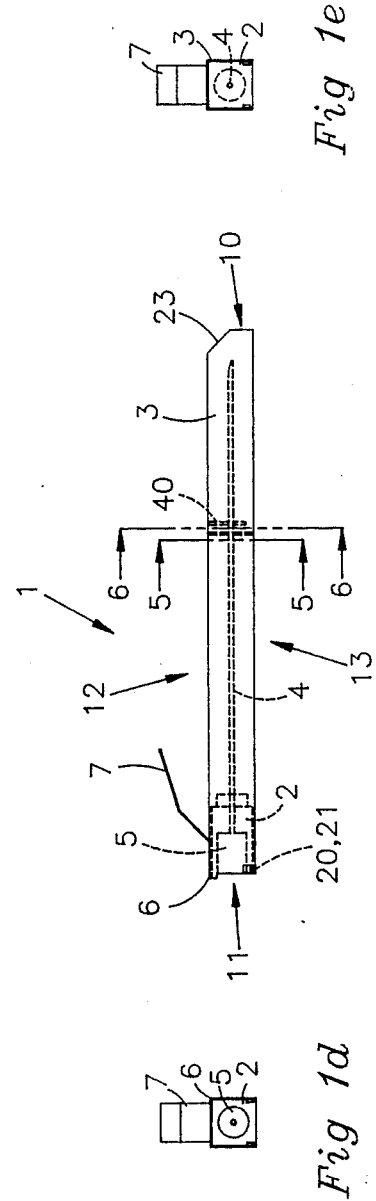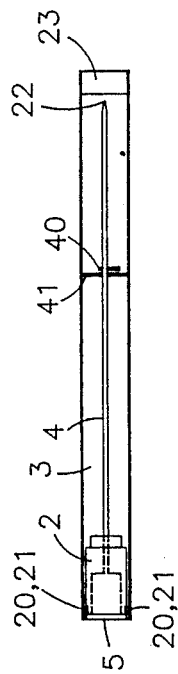

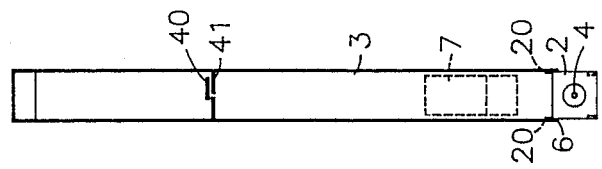
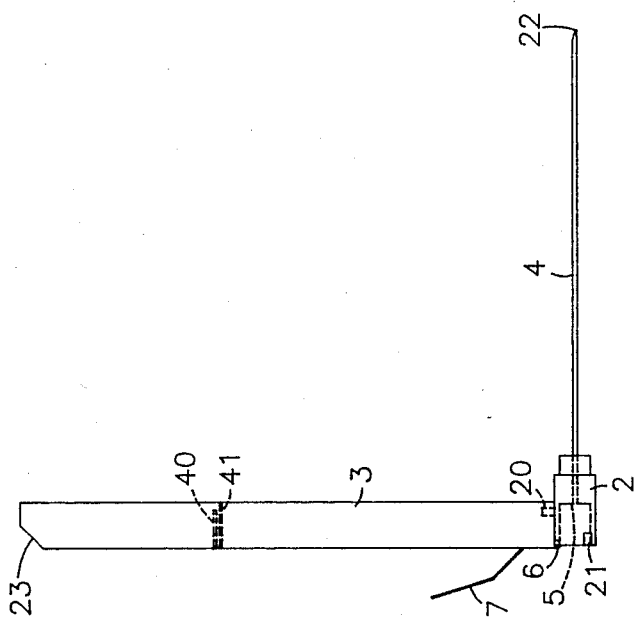
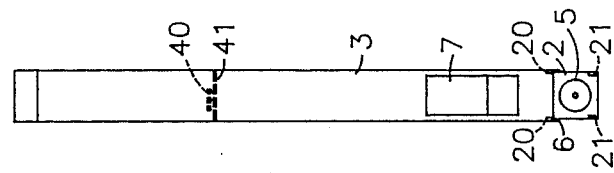

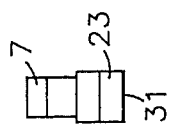
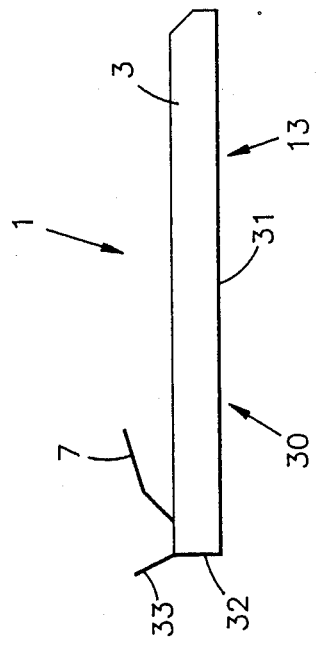
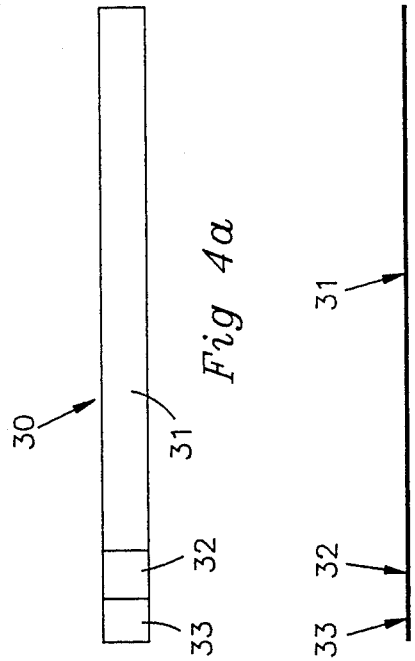
Fig 3c
Fig 3a
Fig 3b
Fig 4a
Fig 4b

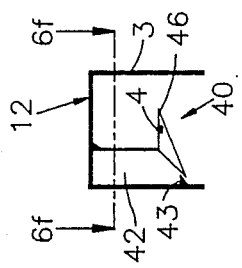
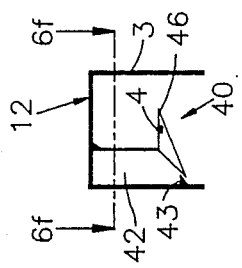
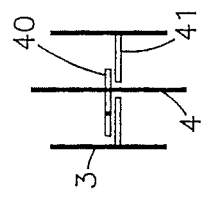
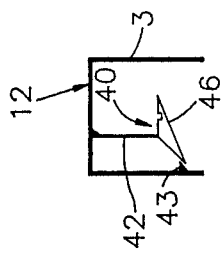
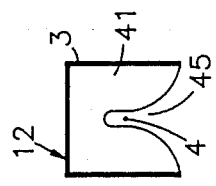
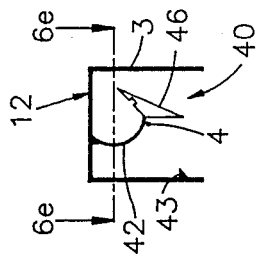
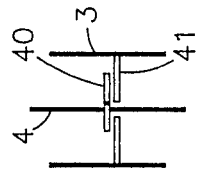

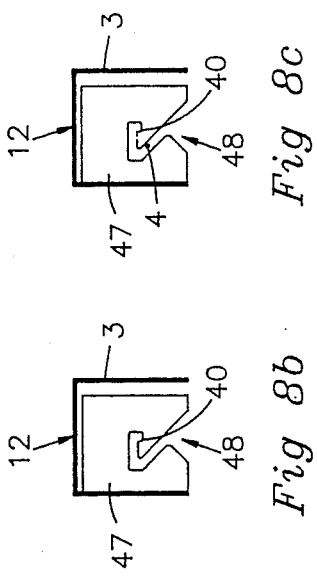
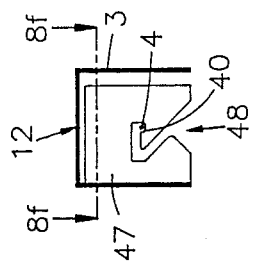
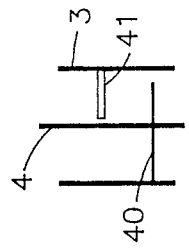
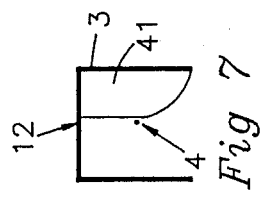
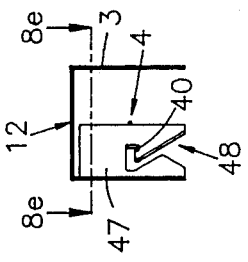
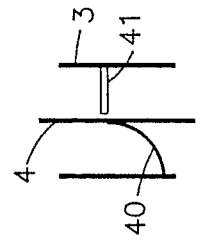

NEEDLE AND SAFETY COVER ASSEMBLY FOR SYRINGES AND THE LIKE

This invention relates to a needle and a safety cover assembly for syringes and the like and, more particularly, relates to an assembly of this type that provides effective protection against accidental needle sticks, maintains the sterility of the needle prior to use, indicates prior use, prevent reuse, and facilitates safe disposal of a contaminated needle.

BACKGROUND OF THE INVENTION

The danger of accidental syringe needle sticks has proven a hazard to healthcare professional since the invention of the syringe. The threat posed by highly toxic medications and communicable diseases such as hepatitis and AIDS, coupled with an increasing safety awareness amidst the healthcare community and the public alike, creates an extreme demand for products which protect patients and professionals alike.

In April 1981, the *American Journal of Medicine* reported approximately one-third of all work-related accidents were needle stick injuries. A more recent study by Biomedical Business International, which was cited in the April 1988 issue of *Medical Device & Diagnostic Industry*, states 800,000 accidental needle sticks were recorded in 1987. With the increased risk posed by the HTLV iii virus (AIDS), this threat becomes more serious, imposing tremendous costs upon individual and healthcare institutions.

Many new products have been developed which attempt to reduce the possibility of accidental needle sticks. Most of these involve a protective sheath which encloses the needle after use. Some of these inventions also relate to the safe isolation and disposal of infected syringe needles.

One such popular device, described in U.S. Pat. No. 4,778,453 (Lopez), is manufactured by ICU Medical, Inc. This device requires a needle extended beyond its normal length. A sliding guard piece resides at the top of the needle adjacent to the syringe body. This guard may be slid down by an operator to cover the tip of the needle, thereby preventing an accidental needle stick. In this arrangement, the healthcare professional must move a hand close to the needle tip while operating the device, thereby potentially increasing the chance for an accidental stick. Additionally, this device does not enclose the entire shaft of the needle, and may not provide an accurate indication of prior use, if the sliding cover does not remain in its protective position, or if it is not moved into its position about the needle tip.

Other recently developed protective devices of interest, although not of direct bearing to the present invention, are disclosed in U.S. Pat. No. 4,747,830to Gloyer, U.S. Pat. No. 4,752,290 to schramm, U.S. Pat. No. 4,758,230 to Rycroft, U.S. Pat. No. 4,758,231 to Harber, U.S. Pat. No. 4,772,272 to Schwartz, U.S. Pat. No. 4,747,835 to Sandhaus, U.S. Pat. No. 4,762,516 to Luther et al., U.S. Pat. No. 4,767,412 to Hyman, and U.S. Pat. No. 4,795,443 to Permenter.

U.S. Pat. No. 4,747,836 to Luther is of interest to the present disclosure. This patent describe a needle guard assembly that comprises two major parts, a needle guard that normally fits over the needle and a separate locking ring mounted on the guard. The needle guard is displaced away from the needle prior to use of the needle, and after such use is replaced over the needle and secured with the locking ring, which rotatably slides over and locks the guard in place over the contaminated needle. However, Luther's assembly does not provide a sterile sealing arrangement which may be used to package the sterile needle prior to use, does not include a fingertab, cannot be operated easily with one hand, does not effectively indicate prior use of the needle, and does not secure the needle within the guard in a manner which substantially discourages reuse. Furthermore, the Luther device must be manipulated by moving a free hand towards the needle tip, potentially increasing the risk of a needle stick.

U.S. Pat. No. 3,658,061 to Hall also describes a needle guard which is placed over the needle in a rotating action. This guard snaps over the needle and thereby prevents accidental stick. It is specifically intended to be used in parenteral fluid administration. Like Luther, this invention also fails to address the opportunities envisioned for a safety guard which may double as the initial needle package, is conducive to one-handed operation, and provides positive indication of needle security and prior use. Hall does not securely lock over the needle to effectively prevent reuse, nor does it prevent an accidental needle stick or contamination during the deployment process of the guard itself. Once again, the deployment of the device may actually increase the chances for a needle stick.

A syringe safety cover which inexpensively and effectively resolves or minimizes the problems associated with the present art would address a large and growing health concern.

OBJECTS OF THE INVENTION

It is an object of this invention to provide, for enclosing a needle for use in the transfer of fluid, a safety cover assembly which provides effective protection against accidental needle sticks and maintains the sterility of the enclosed needle prior to use.

A further object is to provide a safety cover assembly which is adaptable for use with different types of fluid transfer device, including syringes and tubes, regardless of the specific type of connecting means.

A further object is to provide a safety cover assembly which is adaptable for use with needles of varying gauge and length.

A further object is to provide a safety cover assembly that includes a cover portion which may be displaced easily with the same hand that holds the syringe body.

A further object is to provide a safety cover that remains attached to the assembly during deployment of the syringe, but which remains clear of the needle during such deployment.

A further object is to provide a safety cover which is replaceable over the contaminated needle easily and with the same hand that holds the syringe body.

A further object is to provide a safety cover assembly including a cover portion which may be lockingly secured over the contaminated needle to prevent accidental needle sticks and unintentional reuse of the syringe.

A further object is to provide a safety cover which clearly indicates prior use, thereby further preventing unintentional reuse.

A further object is to provide, for enclosing the needle of a syringe, a safety cover assembly which may be safely discarded after use of the needle without significant risk of re-exposing the needle.

The ultimate object is to provide a needle cover assembly that is designed to reduce risk to healthcare professional and patients alike, minimize operational complexity and handling time requirements, operate with little chance for malfunction, be extremely cost-effective, and save lives.

SUMMARY

In carrying out this invention in one form, I provide a needle and cover assembly comprising a base portion with an attached needle, and means for connecting this base protion to a syringe tip or other device for the purpose of transporting fluid via the needle. A cover is attached to the base portion by a hinge, allowing the cover to pivot transversely of the needle in order to either enclose or expose the needle. A fingertab located on the cover near the hinge facilitates this pivoting process. Initially, the safety cover assembly has its needle and attachment means sealed to prevent contamination, with the cover in a down position about the needle. Within the cover is a locking mechanism. This locking mechanism allows the cover to pivot and expose the needle for a single use of the needle, securely retaining the contaminated needle once the cover has been replaced about the needle.

The benefits of the assembly include ease of use, single-handed operation, simplicity, adaptability of the basic design to different needle sizes and attachment means types, sterile enclosure, prior use indication, reuse prevention, safe disposal, and prevention of accidental needle sticks.

BRIEF DESCRIPTION OF THE DRAWINGS

FIG. 1a is a side elevation view of the needle and cover assembly. This figure shows the cover in an initial position with cover disposed about the needle, thereby limiting access to the needle and needle tip.

FIG. 1b is top plan view of the needle and cover assembly of FIG. 1a.

FIG. 1c is a bottom plan view of the needle and cover assembly of FIG. 1a.

FIG. 1d is an end view of the needle and cover assembly of FIG. 1a taken from the back side of the assembly.

FIG. 1e is an end view of the needle and cover assembly of FIG. 1a taken from the front side of the assembly.

FIG. 2a is a side elevation view of the needle and cover assembly showing the cover pivoted into a fully retracted position. The needle is exposed and available for use.

FIG. 2b is an end view of the needle and cover assembly of FIG. 2a taken from the back side of the assembly and showing the top of the cover, fingertab, and attachment means on the base portion.

FIG. 2c is an end view of the needle and cover assembly of FIG. 2a taken from the front end of the assembly and showing the interior of the cover, locking means and guide plate.

FIG. 3a shows the needle and cover assembly with a seal attached to the bottom and back sides, and including a tab to facilitate removal of the seal. This figure shows the cover in an initial position disposed about the needle.

FIG. 3b is an end view of the assembly of FIG. 3a taken at the back side. This figure shows the portion of the seal covering the back end of the base portion and cover, and the tab.

FIG. 3c is an end view of the assembly of FIG. 3a taken at the front side. This figure shows the bottom portion of the seal which covers the longitudinally elongated opening at the bottom of the cover.

FIG. 4a is a top plan view of the seal FIG. 3a shown in a flattened position, separate from the needle and cover assembly.

FIG. 4b is an end view of the seal of FIG. 4a.

FIG. 5 is a sectional view along the line 5—5 of FIG. 1a and showing a guide plate for the needle and cover assembly. FIG. 6a is a sectional view along the line 6—6 of FIG. 1a. This figure shows a locking device of the needle and cover assembly when the cover is in its initial position disposed about the needle.

FIG. 6b is a sectional view of the cover assembly taken along the line 6—6 of FIG. 1a, but illustrating the parts when the cover is in a retracted position exposing the needle. Once the cover is clear of the needle, the locking means is prepared to lockingly engage the needle once the cover is pivoted back down over the needle.

FIG. 6c is a sectional view similar to that of FIG. 6b except showing the cover assembly as the cover is being pivoted back over the needle, with the needle in contact with locking means hook.

FIG. 6d is a sectional view similar to that of FIG. 6c except showing the cover assembly as the cover is completely returned to its initial position about the needle, the locking means hook having flexed back into its original position, thereby retaining the needle within its barb.

FIG. 6e is a sectional view along line 6e—6e of FIG. 6a. This Figure shows a top view of the locking means and guide plate prior to first retraction of the cover and first exposure of the needle.

FIG. 6f is a sectional view along line 6f—6f of FIG. 6d. This figure shows a top view of the locking means and guide plate after the cover has been replaced back around the needle.

FIG. 7 is sectional view along the line 5—5 of FIG. 1a and showing an alternative guide plate for the needle and cover assembly.

FIG. 8a is a sectional view taken at a line corresponding to to the line 6—6 of FIG. 1a but showing a modified locking device of the needle and cover assembly when the cover is in its initial position disposed about the needle.

FIG. 8b is a sectional view of the locking device of FIG. 8a showing the parts when the cover is in a retracted position exposing the needle. Once the cover is clear of the locking means, the resilient locking means plate flexes to its original position, extending to the center of the cover and into the return path of the needle, prepared to lockingly engage the needle once the cover is pivoted back down over the needle.

FIG. 8c is a sectional view of the locking device of FIG. 8a showing the parts as the cover is being pivoted back over the needle, with the needle in contact with a cutout slot in the locking means plate. A portion of the plate may be temporarily flexed, or the entire plate may move slightly, to enable the cover to return back to a position about the needle.

FIG. 8d is a sectional view of the locking device of FIG. 8a showing the parts when the cover is completely returned to its initial position about the needle, the locking means plate retaining the needle within.

FIG. 8e is a sectional view along line 8e—8e of FIG. 8a. This figure shows a top view of the flexed locking means and guide plate prior to first retraction of the cover and first exposure of the needle.

FIG. 8f is a sectional view along line 8f—8f of FIG. 8d. This figure shows a top view of the locking means and guide plate after the cover has been replace back around the needle, subsequent to exposure of the needle, with the needle securely locked within the locking means.

DETAILED DESCRIPTION OF EMBODIMENTS

Figure 9A:
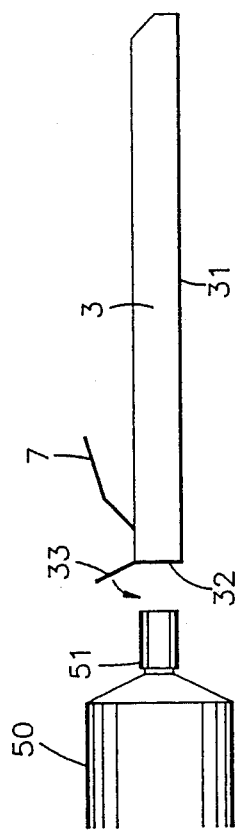
FIG. 9a is a side elevation view of the needle and cover assembly prior to being connected to a syringe and with the cover in its initial positon about the needle and with the seal still in place.

Referring to the embodiment of FIGS. 1a through 1e, the needle and cover assembly 1 depicted therein comprises a needle 4 and two additional elements, a base protion 2 and a connected cover 3. Base portion 2 includes a hollow channel, a portion of which secures needle 4, and has means 5 for attaching the base portion to a syringe body 50 or other fluid transfer device as shown in FIGS 9b and 9c. Cover 3 is attached to base portion 2 by connecting hinge 6, as shown in FIGS. 10a and 10 b. This allows cover 3 to be pivoted with respect to base protion 2 and needle 4, thereby exposing or covering needle 4, as shown in FIGS. 9c through 9e. A fingertab 7 facilitates imparting this pivoting movement. Additionally, a locking mechanism 40, 41 located within cover 3 locks needle 4 within cover 3 once needle 4 has been used.

Base portion 2 is shaped essentially like a box with six sides. Two opposite sides may be considered ends. Back end 11, which is the end attached to a syringe 50, 51 or other fluid transfer mechanism, contains an opening and appropriate attachment means 5. This may accomodate a screw-on type lock, slip-on type lock, or other similar means of attachment. The side opposite attachment means 5, or front end of base poriton 2, has needle 4 extending out from it. Connecting hinge 6 connects base portion 2 with cover 3.

Cover 3 is an elongated body with an open interior, and interior cross-section similar to the exterior cross-section of base portion 2. Cover 3 extends from a region adjacent base portion 2 for a length slightly beyond needle tip 22, so that for one operating cycle it may be pivoted away from and back over needle tip 22 without interference, as shown in FIGS. 9c through 9e. Cover 3 is closed off near needle tip 22, at its far end. Cover 3 has a longitudinally elongated opening along bottom side 13 which is opposite the top side 12 of connecting hinge 6 located to allow needle 4 a passage out of and back into cover 3 interior. Back end 11 of cover 3 located opposite closed off front end 23 is also open to accomodate base portion 2 and any relative movement between base portion 2 and cover 3. Both the opening at the back of cover 3 and the elongated opening have a width that is approximately the same as the width of the cover interior.

Fingertab 7 is located on cover 3 near connecting hinge 6. This is an extension which remains in a substantially fixed position relative to cover 3. It is intended to facilitate opening and closing of cover 3 by pivoting of fingertab 7, rather than direct pivoting of cover 3. Fingertab 7 is positioned and angled to provide for convenient use by the operator, while also avoiding interference with syringe body 50 or operator during use of the needle and cover assembly 1.

Small tabs 20 on the back bottom interior of the sides of cover 3 assist in retaining cover 3 in a down position relative to base portion 2 and needle 4. Tabs 20 are received by indentations 21 located on either side of base portion 2 corresponding to the location of tabs 20 of cover 3 while cover 3 is in its protective position disposed about needle 4, as shown in FIGS. 1a through 1e. When cover 3 is moved into it "up" position exposing needle 4, as shown in FIGS. 2a through 2c, tabs 20 contact the top of base portion 2 and assist in maintaining cover 3 in this temporary positon.

A locking mechanism 40 is provided as an integral part of cover 3 and is located in the interior of cover 3. A locking mechanism is shown in FIGS. 6a through 6f. This locking mechanism 40 comprises a hook 46 which is attached to the ceiling of cover 3 by a flexible arm 42. Hook 46 is initially positioned to one side of needle 4, as shown in FIGS. 6a and 6e, allowing cover 3 to be pivoted away from needle 4 without interference from hook 46. Once needle 4 is no longer contacting the flat side of hook 46, hook 46 is repositioned by means of the shape memory of pliable arm 42 into a second position where it engages a stop 43, as shown in FIG. 6b. This allows cover 3 to be pivoted back down over needle 4 in a manner which causes hook 46 to lockingly engage needle 4, as shown in FIGS. 6c, 6d and 6f. This secures needle 4 and prevents it from being re-exposed.

To assist in keeping needle 4 properly centered while inside cover 3, a guide plate 41, shown in FIG. 5, is included as an integral part of cover 3 and positioned near locking mechanism 40. Guide plate 41 includes a narrow slot 45 open at its lower end for receiving needle 4. Slot 45 is flared at its lower open end to guide needle 4 into slot 45 in the event of possible lateral displacement of needle 4 from the vertical center plane of cover 3. Guide plate 41 is most effectively located near locking mechanism 40, in a position between locking mechanism 40 and base portion 2.

An alternative locking mechanism arrangement, shown in FIGS. 8a through 8f, includes a flexible plate 47 which extends out from a side of cover 3. Plate 47 is preferably of the same plastic material as cover 3 and has an edge, as seen in FIG. 8a, integral with the side wall of the cover 3. Plate 47 may be flexed, to have a flat side against needle 4 prior to the uncovering and use of needle 4, as shown in FIG. 8a and 8e. Once cover 3 is displaced away from needle 4, this alternative lock arrangement 40 is then repositioned by means of the shape memory of the pliable material, thereby moving out to the center of cover 3 interior and into the return path of needle 4, as shown in FIG. 8b. As cover 3 is repositioned back over needle 4 subsequent to use of needle 4, needle 4 is guided into plate 47 within hook-shaped slot 48, in a manner which secures needle 4 in place and prevents cover 3 from further exposing needle 4, as shown in FIGS. 8c, 8d and 8f. A flared guide 41, shown in FIG. 7, extends out from the interior of cover 3 opposite the side of locking plate 47 to prevent sideward displacement of needle 4.

In order to maintain the sterility of needle 4 prior to use, a seal must be maintained about base portion 2 and cover 3, as shown in FIGS. 3e through 3c and 4a and 4b. This includes a seal of the openings at the back 11 of base portion 2, a sealing of the elongated opening at the bottom 13 of cover 3, and a sealing of any openings present at the interface of the base portion 2 and cover 3.

The preferred embodiment includes a single seal 30 which extends from the front bottom of cover 3 rearward to the back bottom of base portion 2 and cover 3, with cover 3 in a down position over needle 4, and then up via a portion 32 to cover the openings at the back end 11 of base portion 2, concluding with an extension which serves as a tab 33 for removal of seal 30, as shown in FIGS. 3a through 3c. A uniform width of the sealing portion of the seal 30 approximately equivalent to the outer width of cover 3 is desirable.

Seal 30 is made of a material which allows the elongated portion of seal 30 at the bottom of cover 3 to be displaced intact, without being broken through, by needle 4 as cover 3 is rotated away from needle 4. A material, such as a bonded paper-foil combination, will prevent rupture of seal 30 by needle 4 and possible contamination of the needle 4 by the unsterilized outer surface of seal 30. Seal 30 is connected by means of an adhesive which facilitates this removal process, but otherwise maintains an effective sterile closure. If desired, seal 30 may be manually removed by simply pulling it off rather than having the relative movement of needle 4 and cover 3 displace seal 30 during the operating cycle.

Figure 9B:
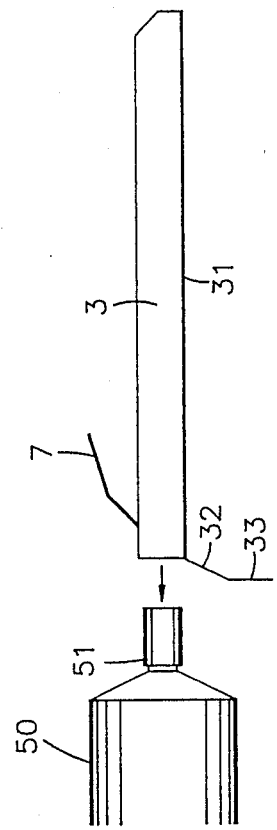
FIG. 9b is view similar to FIG. 9a but with part of seal removed to expose the attachment means located at the back end of the base portion.
Figure 9C:
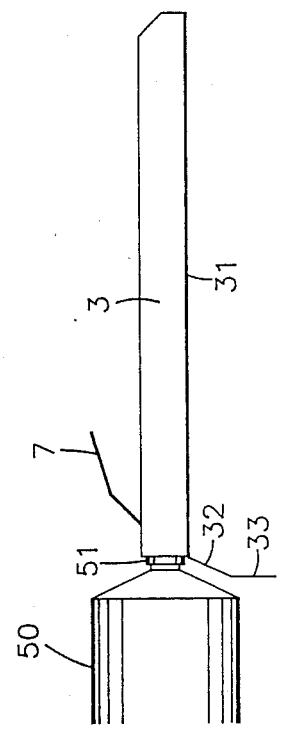
FIG. 9c is a view similar to FIG. 9b but showing the needle and cover assembly in place connected to a syringe attachment means located at the tip of the syringe. The cover remains in its initial position covering the needle.
Figure 9D:
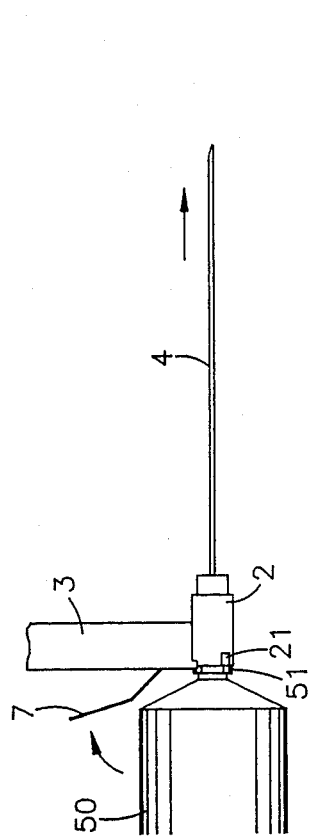
FIG. 9d is a view similar to FIG. 9c, except the cover has been pivoted into its fully retracted position to expose the needle. The needle may now be used to transfer fluid.
Figure 9E:
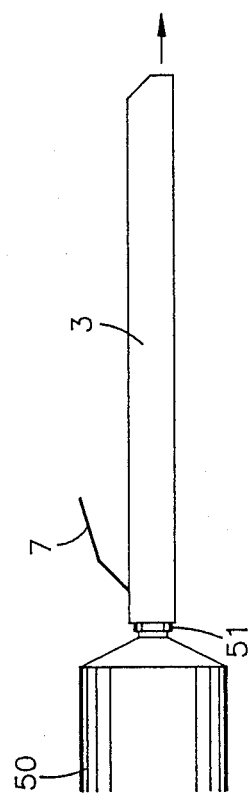
FIG. 9e is a view similar to FIG. 9d except the cover has been returned back to its initial position about the needle. This recovering of the needle after exposure of the needle causes the cover locking means to lockingly engage the needle, preventing a second exposure of the needle.
Figure 10A:
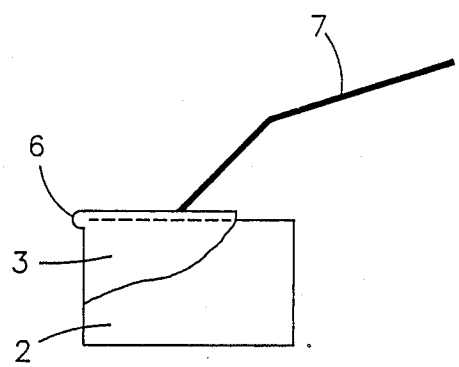
FIG. 10a is an enlarged side plan view of the hinge shown in FIG. 1a, showing a hinge connecting the base portion and cover, with the cover in its initial protective position about the needle.
Figure 10B:
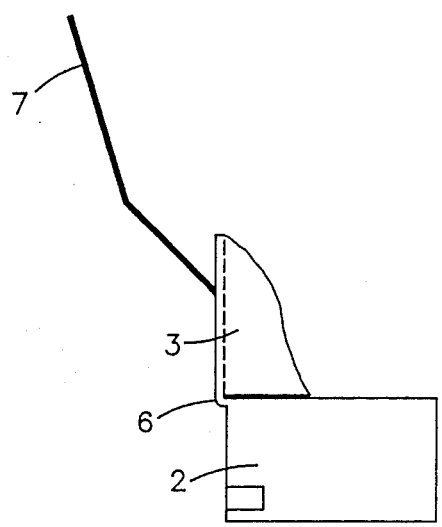
FIG. 10b is an enlarged side plan view of the hinge shown in FIG. 2a, showing the hinge connecting the base portion and cover, with the cover in a retracted position exposing the needle.

In use, the portion of seal 32 over back end 11 of safety cover assembly 1 is removed by pulling on tab 33, as shown in FIGS. 9a and 9b. This allows safety cover assembly 1 to be connected to tip 51 of a syringe body 50 or other fluid transfer mechanism, as shown in FIGS. 9b and 9c. At this time, needle 4 remains sterile, as cover 3 remains down over needle 4, and seal portion 31 securing the elongated opening at bottom 13 of cover 3 remains intact. Optionally, the operator may manually remove the remaining portion of seal 30 at this time, although this will otherwise be performed automatically during the assembly operating cycle.

When the operator is ready, the entire unit 50, 1 is picked up and fingertab 7 is moved with a finger in a direction to pivot cover 3 away from needle 4, as shown in FIGS. 9c and 9d. If the seal over the elongated opening 31 at the bottom of cover 3 is still intact, seal 31 is now displaced from assembly 1 during relative movement of cover 3 and base portion 2. Needle 4 is exposed, and syringe 50 and needle 4 are available for use, as shown in FIG. 9d.

Figure 9F:
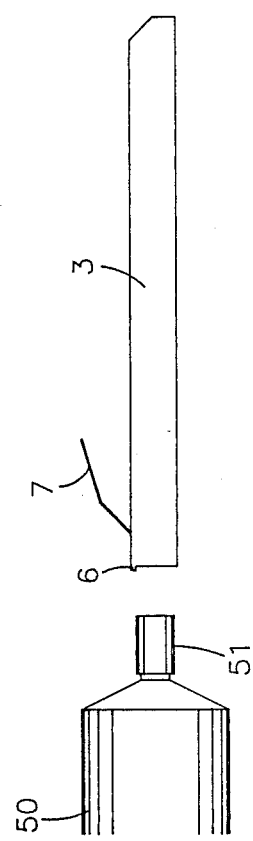
FIG. 9f is a view similar to FIG. 9e except showing the needle and cover assembly removed from the syringe. This may be done to facilitate disposal of the needle and cover assembly. Alternatively, the needle and cover assembly may be disposed still attached to the syringe.

After use, operator pushes fingertab 7 in the reverse direction, pivoting cover 3 back down over contaminated needle 4, as shown in FIG. 9d and 9e. This action locks cover 3 in place over needle 4. The unit 1, 50 may then be discarded, or the safety cover assembly 1 may be detached from syringe body 50 and discarded separately, as shown in FIG. 9f.

While I have shown and described particular embodiments of my invention, it will be apparent to those skilled in the art that various changes and modifications can be made without departing from the spirit of the invention in its broader aspects.

Within the true spirit and scope of my invention, what I claim as new is:

1. A needle and cover assembly comprising:
   A. a base portion having a needle attached at its front end, said needle extending outward and having a tip;
   B. said base portion having an attachment means located at an end opposite said needle for securing said base portion to the tip of a fluid transfer device designed for use with said attachment means;
   C. a needle cover of generally U-shaped transverse cross-section;
   D. a hinge connecting said base portion to said needle cover for enabling said needle cover to be pivoted transverely of said needle;
   E. said needle cover, when in an initial position prior to first use of said needle being disposed about said needle and said base portion, and extending from said base portion to a front end just beyond said needle tip;
   F. said cover having an opening at its back end located opposite said front end, and having a longitudinally elongated opening along the bottom side of said cover between said back and front ends to enable said cover to be pivoted transversely of said needle,
   G. said cover while in said initial position extending along substantially the entire length of said base portion and said needle and also extending about more than half the periphery of said base portion and said needle to such an extent that no part of the base portion or the needle projects laterally substantially beyond said elongated opening;
   H. said needle cover having a fingertab located on the outside of said needle cover and extending outwardly from said needle cover, through which force for pivoting said needle cover relative to said base portion and needle may be applied, and
   I. sealing means attached to said cover and covering said elongated opening and said opening at the back end of the cover for sealing the space within said cover surrounding the needle and the base portion from the surrounding environment when said cover is in its initial position about said needle.

2. A needle and cover assembly comprising:
   A. a base portion having a needle attached at its front end, said needle extending outward and having a tip;
   B. said base portion having an attachment means located at an end opposite said needle for securing said base portion to the tip of a fluid transfer device designed for use with said attachment means;
   C. a needle cover;

D. a hinge connecting said base portion to said needle cover for enabling said needle cover to be pivoted transversely of said needle;
E. said needle cover, when in an initial position prior to first use of said needle being disposed about said needle, and extending from said base portion to a front end just beyond said needle tip;
F. said cover having an opening at its back end located opposite said front end, and having a longitudinally elongated opening along the bottom side of said cover between said back and front ends to enable said cover to be pivoted transversely of said needle;
G. said needle cover having a fingertab located on the outside of said needle cover and extending outwardly from said needle cover through which force for pivoting said needle cover relative to said base portion and needle may be applied,
H. sealing means for protecting the needle and interior of said needle assembly from the outside environment prior to use of said assembly, and
I. locking means for said cover (i) that is ineffective to block pivotal movement of said cover out of said initial position during the first movement of said cover out of said initial position, but (ii) is effective to block pivotal movement of said cover out of said initial position after said first movement of said cover out of said initial position and return of said cover to said initial position.

3. A needle and cover assembling comprising:
A. a base portion having a needle attached at its front end, said needle extending outward and having a tip;
B. said base portion having an attachment means located at an end opposite said needle for securing said base portion to the tip of a fluid transfer device designed for use with said attachment means;
C. a needle cover;
D. a hinge connecting said base portion to said needle cover for enabling said needle cover to be pivoted transversely of said needle;
E. said needle cover, when in an initial position prior to first use of said needle being disposed about said needle, and extending from said base portion to a front end just beyond said needle tip;
F. said cover having an opening at its back end located opposite said front end, and having a longitudinally elongated opening along the bottom side of said cover between said back and front ends to enable said cover to be pivoted transversely of said needle;
G. said needle cover having a fingertab located on the outside of said needle cover and extending outwardly from said needle cover, through which force for pivoting said needle cover relative to said base portion and needle may be applied, and
H. locking means for said cover (i) that is ineffective to block pivotal movement of said cover out of said initial position during the first movement of said cover out of said initial position, but (ii) is effective to block pivotal movement of said cover out of said initial position after said first movement of said cover out of said initial position and return of said cover to said initial position.

4. The assembly of claim 3 in which said base portion attachment means allows said base portion to be secured to a syringe or other fluid transfer device having a slip-on type tip.

5. The assembly of claim 3 in which said base portion attachment means allows said base portion to be secured to a syringe or other fluid transfer device having a screw-on type tip.

6. The assembly of claim 3 in which said hinge comprises a flat connecting joint having a width approximating the width of said base portion.

7. The assembly of claim 3 in which said hinge has substantially no length.

8. The assembly of claim 3 in which said fingertab is connected to said cover in such a manner that the angle between said fingertab and the longitudinal axis of said cover remains substantially constant during said pivoting.

9. The assembly of claim 3 in which said hinge allows said needle cover to pivot transversely of said needle with said needle cover motion being in substantially one plane, thereby minimizing sideward deviation of said needle cover and said fingertab during pivoting movement.

10. The assembly of claim 3 in which said front end is closed off to further prevent access to said needle when said cover is in a protective position disposed about said needle.

11. The assembly of claim 3 further comprising a sealing means with material shaped to cover substantially all of said bottom side and said back end of said base portion and cover, including said attachment means, said longitudinally elongated opening, and openings present at the interface of said base and cover portions, when said cover is in an initial position about said needle.

12. The seal of claim 11 in which said material is of sufficient resistance to tearing that said needle, during said pivoting of said cover away from said needle, pushes said seal off of said cover rather than breaking through said seal material.

13. The assembly of claim 3 in which said locking means comprises:
(a) a hook having a side facing generally away from said opening, a bottom side facing generally toward said opening, and a barb generally facing away from said opening, and;
(b) means for biasing said hook into a locking position where said needle is retained by said barb when said cover is moved into said protective position.

14. The assembly of claim 13 in which said barb has a slight extension extending partially about said needle when said hook is in a locking position relative to said needle, thereby effecting secure locking retention of said needle once said needle is positioned within grasp of said barb.

15. The assembly of claim 13 in which said biasing means includes a flexible resilient arm attached to said cover, said arm being flexed while said needle cover is initially covering said needle, so that said hook rests against said needle in a position which allows said locking means to move free of said needle as said cover is pivoted away from said needle.

16. The assembly of claim 13 in which:
(a) said biasing means includes a flexible arm attached to said cover at a predetermined point opposite said opening, and;
(b) said flexible arm and hook, once said cover is pivoted away from its initial position covering said needle, return back to a reset position with said arm substantially unflexed and said barb generally facing said predetermined point.

17. The assembly of claim 13 in which said biasing means includes a flexible, resilient arm coupled to said hook for moving said hook toward a position for effecting locking of said needle once said cover is pivoted away from said needle.

18. The assembly of claim 3 in which said locking means comprises a hook that lockingly engages said needle as said needle cover is pivoted back into position over said needle subsequent to use of said needle.

19. The assembly of claim 3 further comprising a guide plate positioned inside said cover and having an opening for receiving said needle and for restricting the movement of said needle approximately to a predetermined plane, while said needle is in contact with said guide plate, thereby countering any sideward forces upon said needle by said locking means.

20. The assembly of claim 3 in which said locking means comprises:
   A. a flexible resilient plate that is held in a retracted position by said needle when the cover is in its initial position prior to exposure of said needle, and in which;
   B. said plate is adapted to move into a position intersecting the path of said needle in response to pivoting of the cover out of its initial position to expose said needle;
   C. said plate includes a locking groove shaped to receive and thereafter retain said needle when said cover is returned to its initial position about said needle.

21. The assembly of claim 20 in which said locking groove has a hook-shaped profile which displaces said needle and said cover slightly away from the plane of said pivoting action, to thereby direct movement of said needle relative to said cover into a position within said locking groove to securely engage and retain said needle.

22. The assembly of claim 20 in which said locking means plate has an extension, which extends partially about said needle when said locking means plate is in a locking position relative to said needle, thereby effecting secure locking retention of said needle once said needle is positioned within said locking groove.

23. The assembly of claim 3 further comprising a guide plate positioned inside said cover and having a flat edge guiding said needle and for restricting the movement of said needle approximately to a predetermined plane, while said needle is in contact with said guide plate, thereby countering any sideward forces upon said needle by said locking means.

24. A method of deploying the needle and cover assembly of claim 2 in conjunction with a fluid transfer device adapted for use with said assembly comprising the following steps:
   A. Removing said sealing means from the area of said attachment means of said needle and cover assembly base portion;
   B. Connecting said needle and cover assembly to said fluid transfer device;
   C. While holding said fluid transfer device, urging said assembly fingertab in a direction which causes said cover to pivot away from said needle, thereby displacing said sealing means covering said elongated opening and pivoting said needle cover clear of said needle, thus preparing said fluid transfer device and said needle and cover assembly for deployment;
   D. Using said device and said needle to transfer fluid;
   E. Urging said assembly fingertab in a direction which causes said needle cover to pivot into a position back over said needle.

25. The method of claim 24 in which said device is a syringe.

26. The method of claim 24 in which said device is a fluid transfer tube.

27. The method of claim 24 in which steps C, D and E are performed with one hand.

28. The assembly of claim 3 in which said locking means includes a locking member that lockingly engages said needle when said cover is returned to its initial position over said needle after a first movement of said cover out of said initial position.

* * * * *